(12) United States Patent
Sanders et al.

(10) Patent No.: US 11,493,783 B2
(45) Date of Patent: Nov. 8, 2022

(54) METHOD OF FITTING SCLERAL AND CORNEO-SCLERAL LENSES

(71) Applicant: Visionary Optics LLC, Oak Brook, IL (US)

(72) Inventors: Donald Sanders, Oakbrook, IL (US); Gregory DeNaeyer, Upper Arlington, OH (US)

(73) Assignee: Visionary Optics LLC, Oak Brook, IL (US)

( * ) Notice: Subject to any disclaimer, the term of this patent is extended or adjusted under 35 U.S.C. 154(b) by 492 days.

(21) Appl. No.: 16/528,272

(22) Filed: Jul. 31, 2019

(65) Prior Publication Data

US 2020/0041817 A1    Feb. 6, 2020

Related U.S. Application Data

(60) Provisional application No. 62/712,354, filed on Jul. 31, 2018.

(51) Int. Cl.
| | |
|---|---|
| *G02C 7/04* | (2006.01) |
| *G01B 11/16* | (2006.01) |
| *G06T 7/50* | (2017.01) |
| *G01B 11/25* | (2006.01) |
| *G02C 7/02* | (2006.01) |

(52) U.S. Cl.
CPC ............ *G02C 7/047* (2013.01); *G01B 11/167* (2013.01); *G01B 11/2513* (2013.01); *G02C 7/024* (2013.01); *G02C 7/049* (2013.01); *G06T 7/50* (2017.01)

(58) Field of Classification Search
CPC .............................. G01B 11/167; G02C 7/047
USPC ........................................................ 351/219
See application file for complete search history.

(56) References Cited

U.S. PATENT DOCUMENTS

| | | | |
|---|---|---|---|
| 7,862,178 B2 | 1/2011 | Shyu et al. | |
| 8,366,272 B1 | 2/2013 | Myhill et al. | |
| 2010/0128224 A1* | 5/2010 | Legerton | G02C 7/047 351/247 |
| 2010/0271589 A1* | 10/2010 | Legerton | G02C 7/04 351/159.02 |
| 2017/0082869 A1 | 3/2017 | Sindt et al. | |

(Continued)

FOREIGN PATENT DOCUMENTS

| | | | | |
|---|---|---|---|---|
| CN | 101404954 A | * | 4/2009 | ............... A61B 3/00 |
| KR | 101215738 B1 | * | 12/2012 | |
| WO | WO2018069665 | | 4/2018 | |

OTHER PUBLICATIONS

Denaeyer, G. et al, "Correlation of corneal and scleral topography in cases with ectasias and normal corneas: The SSSG study", J. Cont. Res. Sci., vol. 3(1), pp. e10-e20, (May 9, 2019).

(Continued)

*Primary Examiner* — James R Greece
(74) *Attorney, Agent, or Firm* — McHale & Slavin, P.A.

(57) ABSTRACT

A method for fitting contact lenses. More specifically, methods of fitting scleral or corneo-scleral lenses utilizing data or patterns observed on a corneal topography examination to improve the fit of scleral lenses or corneo-scleral lenses. The method may use quadrant specific fitting set lenses or regular toricity in unusual portions of the lens to define which patients may most benefit from such lenses.

12 Claims, 13 Drawing Sheets
(8 of 13 Drawing Sheet(s) Filed in Color)

(56) References Cited

U.S. PATENT DOCUMENTS

2017/0123230 A1  5/2017  Carrasquillo et al.
2018/0107021 A1  4/2018  Bishop et al.

OTHER PUBLICATIONS

Denaeyer, G. et al, "Qualitative assessment of scleral shape patterns using a new wide field ocular surface elevation of topographer: The SSSG study", J. Cont. Res. Sci., vol. 1(1), pp. 12-22, (Nov. 16, 2017).

Macedo-de-Araujo, R. et al, "Relationship of placido corneal topography data with scleral lens fitting parameters", Contact Lens and Anterior Eye, vol. 42, pp. 20-27, (2019).

Pinero, D. et al, "Differences in comeo-scleral topographic profile between healthy and keratoconus corneas", Contact Lens and Anterior Eye, vol. 42, pp. 75-84, (2019).

* cited by examiner

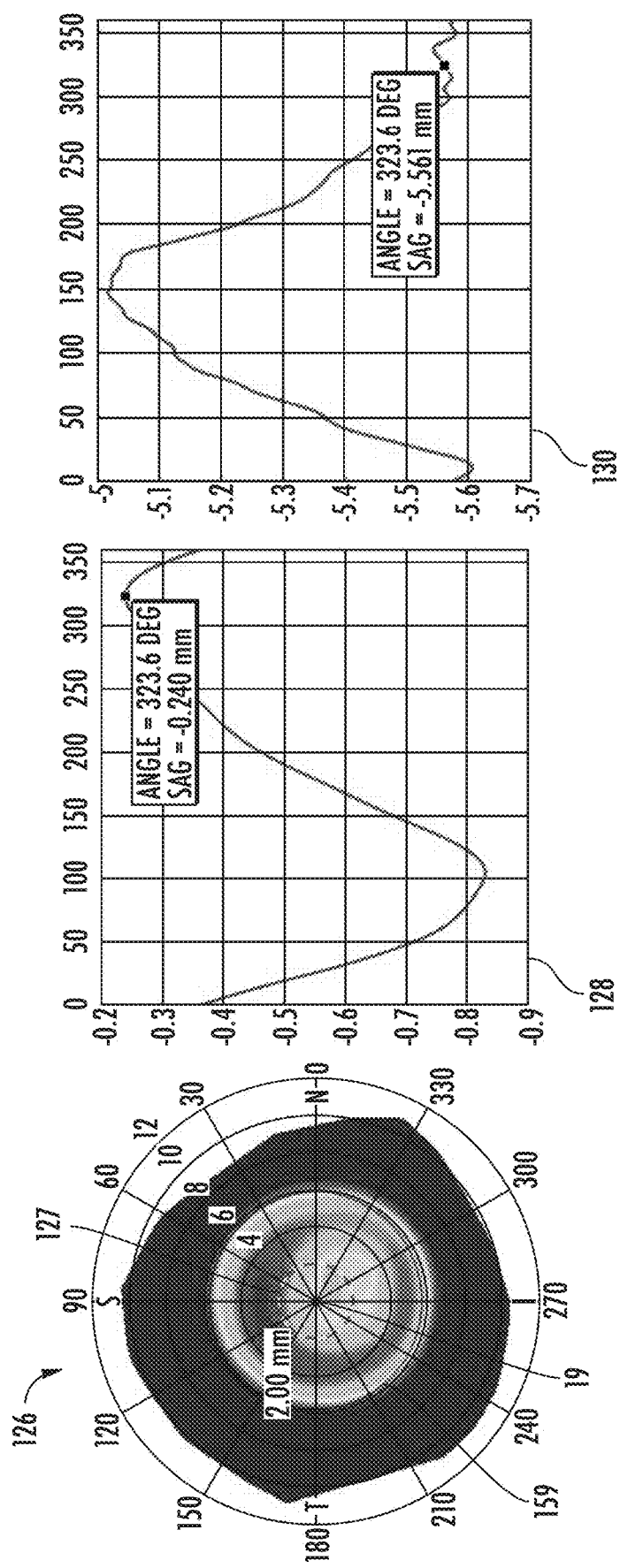

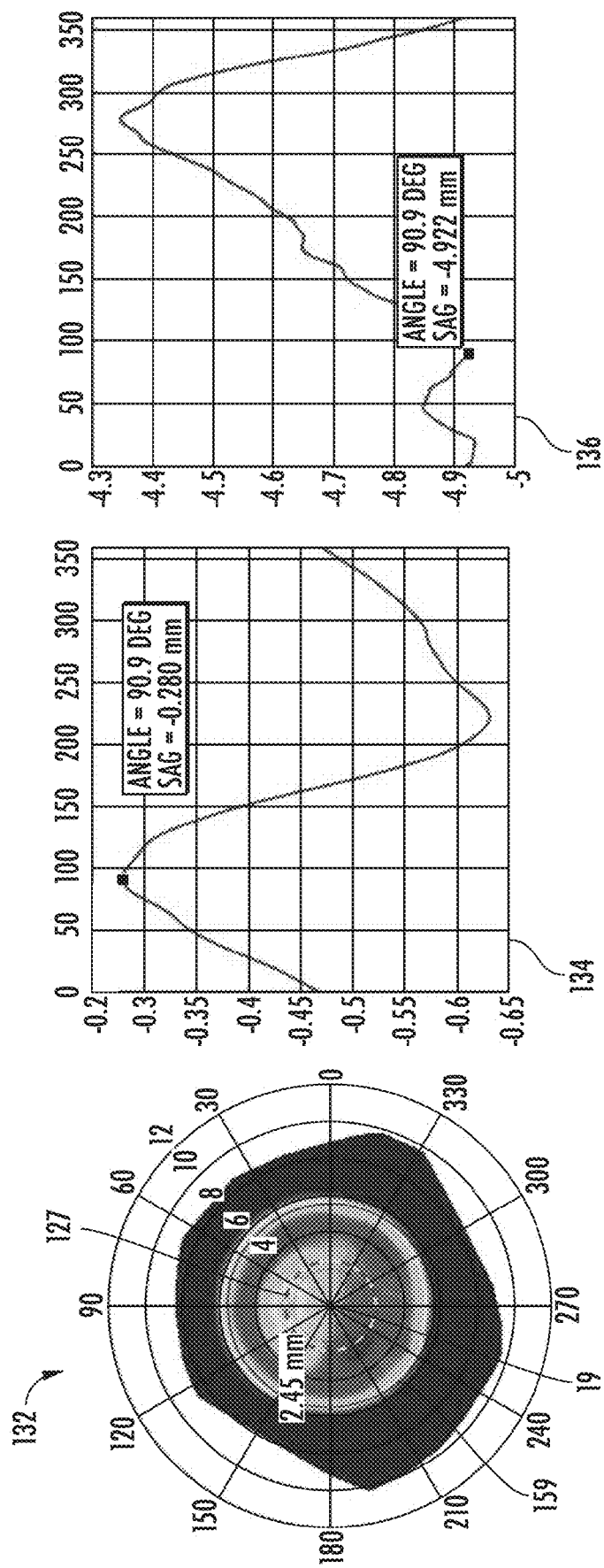

METHOD OF FITTING SCLERAL AND CORNEO-SCLERAL LENSES

PRIORITY CLAIM

In accordance with 37 C.F.R. § 1.76, a claim of priority is included in an Application Data Sheet filed concurrently herewith. Accordingly, the present invention claims priority to U.S. Provisional Patent Application No. 62/712,354, entitled "METHOD OF FITTING SCLERAL AND CORNEO-SCLERAL LENSES", filed Jul. 31, 2018. The contents of the above referenced application is incorporated herein by reference.

FIELD OF THE INVENTION

The disclosure relates generally to contact lenses. More specifically, the disclosure relates to scleral, corneo-scleral, or scleral and corneo-scleral lenses. The invention relates to a method for improving the initial fit of scleral and/or corneo-scleral lenses; more specifically, the present invention relates to methods of fitting scleral or corneo-scleral lenses which utilize patterns observed on a corneal topography examination to improve the fit of scleral lenses or corneo-scleral lenses.

DESCRIPTION OF THE RELATED ART

Some patients require contact lenses shaped such that the edge of the contact lens rests on the sclera of the eye. The sclera, the white fibrous opaque layer of the eye, with the cornea, forms the outer covering of the eyeball. The sclera, in turn, is covered by a translucent spongy layer known as conjunctiva, which covers the front surface of the sclera and wraps around to cover the inner surface of the eyelid. Contact lenses made of rigid gas permeable (RGP) material having an edge that rests on the sclera and having virtually no contact with the cornea are called scleral lenses. Scleral lenses are intended to vault over the entire cornea, including the corneal-scleral/conjunctival junction, which is referred to as the limbus. This limbal area contains stem cells which are critical to ocular health. It is currently recognized that significant touch of a scleral lens to the limbal area may damage sensitive stem cells. Furthermore, too much vault of scleral lenses over the limbal area can excessively separate the limbal stem cells from their primary source of oxygenation, the air anterior to the lens. Accordingly, no vault over the limbus or too much vault can be detrimental.

Approximately 100-150 microns of limbal clearance is currently considered optimal. The back surface of the scleral lens is intended to touch uniformly over the scleral/conjunctival surface. This area of scleral lens touch is referred to as the landing zone. The back surface of a standard scleral lens over the cornea and the limbus is virtually always rotationally symmetrical (no toricity, no quadrant specific toricity) because that portion of the lens is not touching the eye. Up until now, there has been no way to routinely and accurately measure the fit in this area 360° around, nor has it been understood how to improve the fit in this area. This is unlike the landing zone, where the goal is to attempt to match the fit of the scleral lens of the eye to the ocular surface.

Some lens designs are configured to rest partly on the cornea and partly on the sclera. These types of lenses are known as corneo-scleral lenses. Historically, corneo-scleral and scleral contact lenses are difficult to fit. A major indication for use of scleral lenses includes patients with corneal irregularities, such as keratoconus, which is characterized by a bulging and thinning of a portion of the cornea. A recent study of patients scheduled for sclera lens fitting has shown that the scleral surface had an irregular shape in almost ⅔ of the cases, see DeNaeyer G, Sanders D, van der Worp E, et al. Qualitative assessment of scleral shape patterns using a new wide field ocular surface elevation topographer. J Cont Lens Res Sci 2017; 1(1):12-22.

Past methods of fitting contact lenses that are fit on the cornea include keratometric measurements to measure the eye (which only measures four distinct points at 3 mm from the center of the cornea), corneal topography instruments and empirical (trial and error) methods using trial lenses, usually from a fitting set. While these methods may be sufficient for fitting corneal contact lenses, they are not optimal for fitting corneo-scleral or scleral contact lenses. Methods employing keratometric measurements to measure the eye, or corneal topography instruments, are unable to measure the scleral/conjunctival surface upon which these lenses rest. As a result, these methods have not proven useful for fitting corneo-scleral or scleral contact lenses. Some studies have shown a lack of consistency between corneal and scleral findings, Macedo-de-Araújo, R J, Amorim-de-Sousa, A, Queirós et. al., Relationship of placido corneal topography data with scleral lens fitting parameters. Cont Lens Anterior Eye 2018 Jul. 25; Piñero DP, Martinez-Abad A, Soto-Negro R, et al. Differences in corneo-scleral topographic profile between healthy and keratoconus corneas. Cont Lens Anterior Eye 2018 May 22.

Standard corneal topography instruments are cost effective and readily available in eye care practices that fit contact lenses. There are advanced instruments available that can measure the scleral/conjunctival surface; in some cases, providing scleral topography as well as corneal topography measurements. Unfortunately, these instruments can be very expensive, which limits their widespread use.

The method of fitting scleral lenses and corneo-scleral lenses using trial lenses from a fitting set is the most common method currently employed to fit these types of lenses. Due to the irregular nature of the scleral/conjunctival surface in many of these cases, trial lens fitting frequently becomes a time consuming, labor intensive and expensive process. In fact, use of trial fitting sets is often described as more of an art than a science. Trial lens fitting sets are limited in terms of the number of lenses and parameters, which frequently results in the practitioner ordering a patient lens and hoping for a reasonable fit. Trial lenses in fitting sets currently contain spherical or regular (symmetrical) toric peripheral haptic lenses. Lenses with asymmetrical designs are not used. Furthermore, the toric peripheral haptics portion of the lens typically begins over the portion of the lens that is meant to be in contact with the eye (the landing zone). A number of laboratories offer the ability to design a "quadrant specific" lens for an individual patient; one that has a different sagittal height (SAG) value in two axes 180° apart. These are usually ordered based upon clinical observation, or because of findings from an instrument that measures the scleral/conjunctival surface. It is generally believed that these are not usually necessary and/or not observed with sufficient frequency to warrant incorporation into a fitting set.

Commonly, lenses have to be remade (remanufactured) multiple times over a period of weeks, or even months, to get an acceptable fit. In spite of not charging extra to remake lenses within 90 days of initial purchase, it is believed that approximately 10% of scleral lens purchases are returned for cash credit. Presumably, scleral lens purchase returns are due to an inability to obtain a good patient fit.

Accordingly, methods and procedures that speed up and improve this process to make it more efficient for the practitioner, and expeditiously get the patient the correct fit contact lens they need for visual rehabilitation would be beneficial.

BRIEF SUMMARY OF THE INVENTION

The present invention relates to a method for improving the initial fit of scleral and/or corneo-scleral lenses. A unique method of determining if cornea information/data may be used for fitting scleral or corneo-scleral lenses, referred to generally as scleral/corneo-scleral lens fitting determination process is described. In addition, a unique method of fitting scleral or corneo-scleral lenses using corneal topography data is also described. Both methods allow eye care professionals that do not have access to the new and expensive scleral topography systems to improve and accelerate scleral or corneo-scleral lens fitting, particularly in patients suffering from keratoconus, and other diseases with areas of corneal elevation/steepness and other irregularities.

The invention may also include sclera or corneo-scleral fitting lens set comprising one or more quadrant specific lens, which include any lens that have 60μ to 500μ difference in sagittal height on a back surface of the quadrant specific lens in any two points 180° apart, equidistant from and at least 5.5 mm from the corneal center.

The invention may also include a sclera or corneo-scleral fitting lens set comprising one or more toric lens having at least 60μ to 500μ difference in sagittal height on a posterior lens surface in any two points 90° apart, equidistant from, and within 5 mm from the corneal center.

Accordingly, it is an objective of the invention to disclose a method which improves scleral lens fitting.

It is a further objective of the invention to disclose a method which improves corneo-scleral lens fitting.

It is yet another objective of the invention to provide methods of fitting scleral lenses which utilize patterns observed on a corneal topography examination to improve the fit of the scleral lenses.

It is a further objective of the invention to provide methods of fitting corneo-scleral lenses which utilize patterns observed on a corneal topography examination to improve the fit of the corneo-scleral lenses.

It is a still further objective of the invention to teach accelerated scleral lens fittings in patients with Keratoconus using findings or data from corneal topography.

It is a further objective of the invention to teach accelerated corneo-scleral lens fittings in patients with Keratoconus using findings or data from corneal topography.

It is yet another objective of the invention to teach accelerated scleral lens fittings in patients with eye diseases having areas of corneal elevation/steepness using findings or data from corneal topography.

It is a still further objective of the invention to teach accelerated corneo-scleral lens fittings in patients with eye diseases having areas of corneal elevation/steepness using findings or data from corneal topography.

It is yet another objective of the invention to teach accelerated scleral lens fittings in patients with eye irregularities using findings or data from corneal topography.

It is a still further objective of the invention to teach accelerated corneo-scleral lens fittings in patients with eye irregularities using findings or data from corneal topography.

It is a further objective of the invention to teach a method of using quadrant specific fitting set lenses which is more feasible by defining which patients may most benefit from such lenses.

It is yet another objective of the invention to teach methods which may be used to reduce or eliminate the need for trial lenses associated with scleral lenses.

It is a still further objective of the invention to teach methods which may be used to reduce or eliminate the need for trial lenses associated with corneo-scleral lenses.

It is a further objective of the invention to teach methods which may be used to reduce costs associated with scleral lens fittings.

It is yet another objective of the invention to teach methods which may be used to reduce costs associated with corneo-scleral lens fittings.

It is a further objective of the invention to teach methods which may be used to reduce the time associated with scleral lens fittings.

It is yet another objective of the invention to teach methods which may be used to reduce the time associated with corneo-scleral lens fittings.

It is yet another objective of the invention to teach diagnostic fitting sets for scleral or corneo-scleral lenses.

It is a further objective of the invention to teach a quadrant specific sclera lens.

It is a further objective of the invention to teach a quadrant specific corneo-scleral lens.

It is yet another objective of the invention to teach a toric fitting sclera lens.

It is yet another objective of the invention to teach a toric fitting corneo-scleral lens.

It is a further objective of the invention to teach a sclera fitting set with one or more quadrant specific sclera lens.

It is a further objective of the invention to teach a corneo-scleral fitting set with one or more quadrant specific corneo-scleral lens.

It is yet another objective of the invention to teach a sclera fitting set with one or more toric fitting sclera lens.

It is yet another objective of the invention to teach a corneo-scleral fitting set with one or more toric fitting corneo-scleral lens.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE DRAWINGS

The patent or application contains at least one drawing executed in color. Copies of this patent or patent application publication with color drawings will be provided by the Office upon request and payment of the necessary fee.

FIG. 4A is a color-coded cornea map with cone apex at 2 mm radius;

FIG. 4B is a corneal shape plot graph at 2 mm radius;

FIG. 4C is a scleral shape plot graph at 8 mm radius;

FIG. 5A is a color-coded cornea map with cone apex at 2.45 mm radius;

FIG. 5B is a cornea shape plot graph at 2.45 mm radius;

FIG. 5C is a sclera shape plot graph at 8 mm radius;

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

The present invention relates to methods for improving the initial fit of scleral and/or corneo-scleral lenses. The methods were derived by evaluating various patients. Data was collected on a series of individuals, each known to have corneal irregularities and diagnosis. Each of the patients underwent a corneo-scleral topography examination. Data was also derived from other source, such as Optical Coherence Tomography (OCT), if such tests allowed for a similar analysis. Corneal pathology was displayed on a corneal map, which was used to define axis, position, and/or magnitude of the pathology. A corneal shape plot may be used to refine this information.

Figures 1A, 1B:
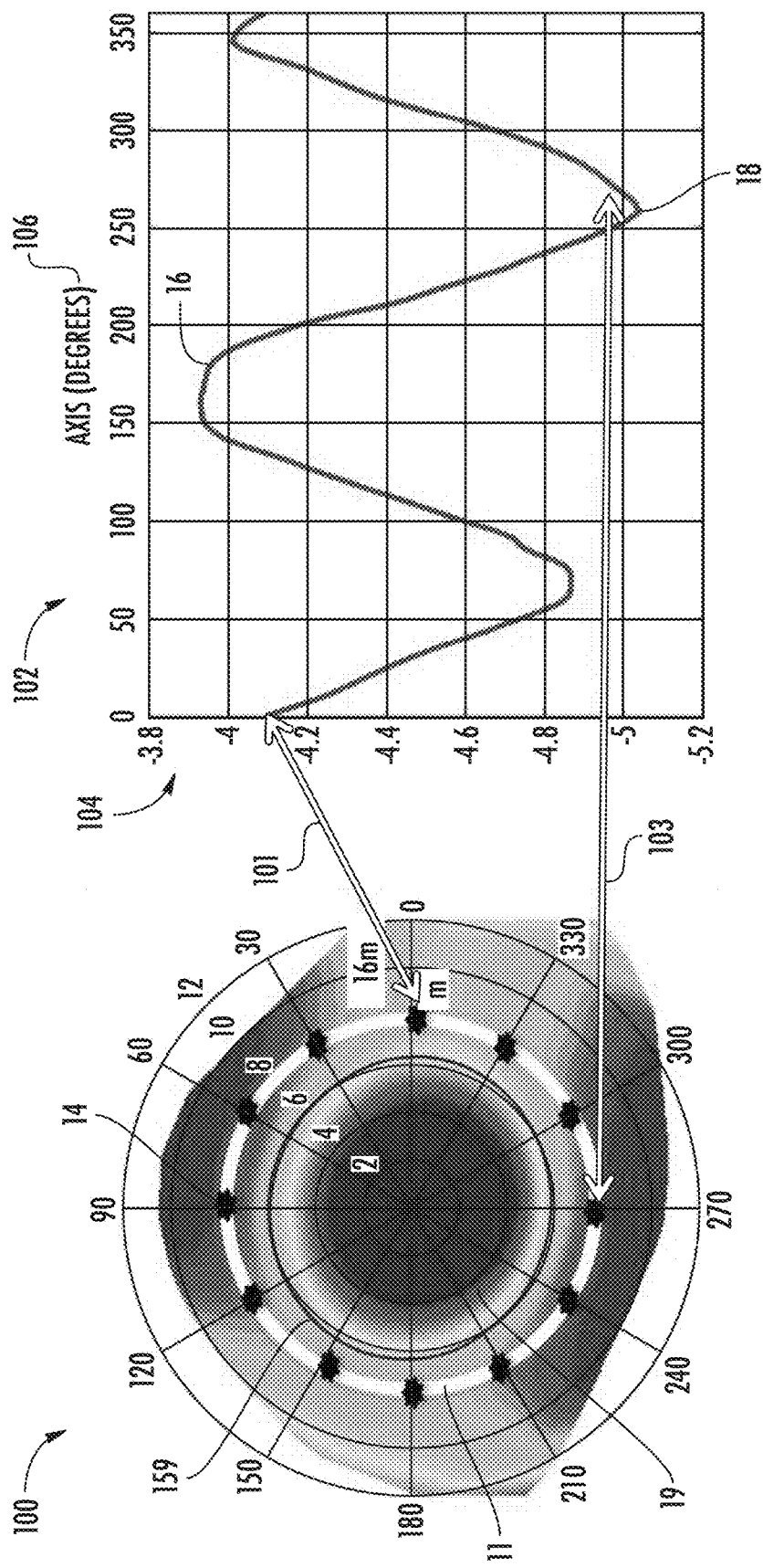
FIG. 1A illustrates a sclera elevation map.
FIG. 1B illustrates a corresponding scleral shape plot graph.

Mapping of the sclera, see FIG. 1A, was used to compare and correlate specific information about the shape of the cornea derived from corneal topography providing information on conjunctiva/sclera based on the maps generated by the ocular surface profiler. FIG. 1A illustrates an embodiment of a topographical image of an eye, illustrated as a color-coded scleral elevation map 100. The qualitative scleral elevation map 100 displays a color-coded map of scleral elevation using polar coordinates. The numbers 2, 4, 6, 8, 10, and 12 on the color-coded scleral elevation map 100 represent the number, in millimeters (mm), to the center of the cornea. For example, "12" represents 12 mm to the center of the cornea (24 mm diameter). The 16 mm diameter circumference is outlined in the white circle 11, and sample points are shown as black stars 14. The scleral shape plot derived from data from the 16 mm diameter circumference demonstrating the sagittal height of the eye (SAG) value at each point along this circumference from 0° to 360° is shown as a circumferential scleral shape plot 102, see FIG. 1B. The high points of this graph demonstrate elevated areas 16 of the eye surface, and the depressions 18 represent the low points.

The center area of the cornea in FIG. 1A is a uniform color because the scale has been optimized for the conjunctival/scleral surface. The center of the cornea is illustrated on the figures as the center point 19. Sagittal height of the eye (SAG values) was determined at a fixed 16 mm diameter from the corneal center in this example. The color-coded scleral elevation map 100 illustrates a depressed area, with a higher sagittal height (blue), alternating with a more elevated area, generating a lower SAG (green, yellow, or red color) approximately every 90°. The circumferential scleral shape plot 102 is made with the sagittal height of the eye (SAG, Y-axis 104) plotted against the meridional axis (X-axis, 106) 360° for any radius or diameter from the center of the cornea. Each data point collected on the scleral elevation map 100 was plotted to generate the circumferential scleral shape plot 102. Arrows 101 and 103 show similar points on the two maps 100 and 102.

Figures 2A, 2B, 2C, 2D:
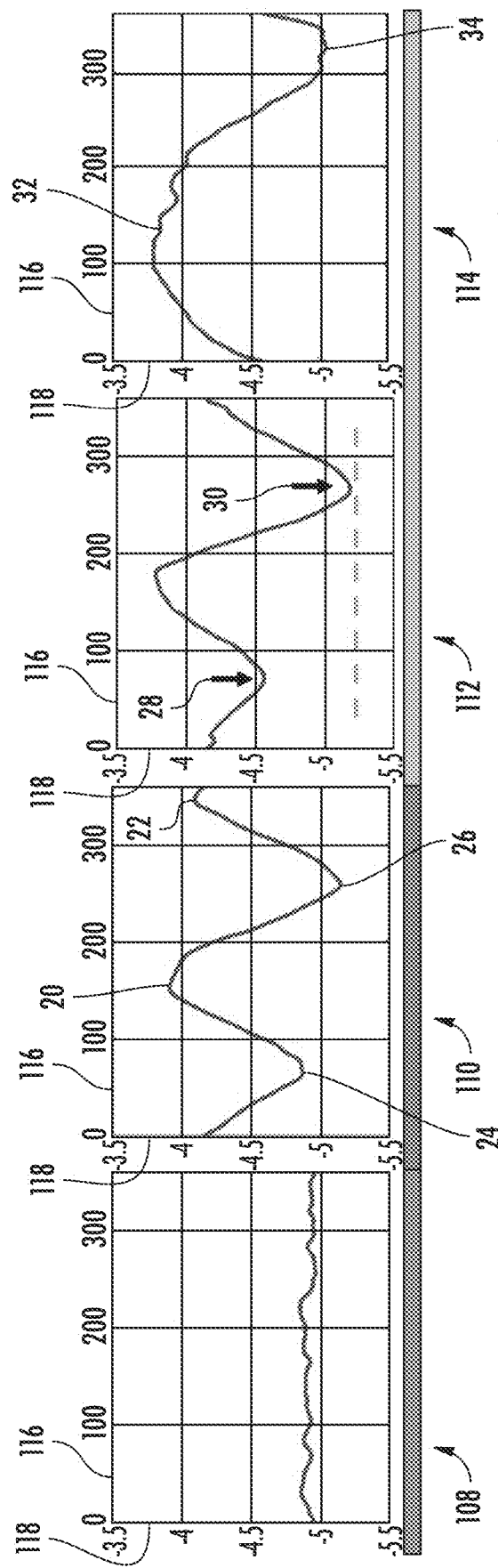
FIG. 2A is a scleral shape pattern, illustrating a spherical shape.
FIG. 2B is a scleral shape pattern, illustrating a toric shape.
FIG. 2C is a scleral shape pattern, illustrating an asymmetric depression shape.
FIG. 2D is a scleral shape pattern, illustrating an asymmetric periodicity not 180° shape.

Referring to FIGS. 2A-2D, various scleral shape patterns are known, including spherical shape pattern 108, FIG. 2A, a toric shape pattern 110, FIG. 2B, asymmetric, depression or elevation shape pattern 112, FIG. 2C, and asymmetric, periodicity not 180° pattern 114, FIG. 2D. Toric shapes have two elevations 20, 22 and two depressions 24, 26 throughout 360°. The repeating pattern (or periodicity) occurs every 180°. The asymmetrical depression in FIG. 2C is shown at 28 and 30. Asymmetrical elevations would also be included in this pattern group. With regards to the graph shown in FIG. 2D, instead of two elevations and two depressions over 360°, there is only one of each (elevation 32, depression 34). The periodicity is 360°. This group encompasses cases with periodicity other than 180°. In each of FIGS. 2A-2D, the X-axis 116 is the axis of the data points on a polar scale. The Y-axis 118 is SAG data from a circumlinear curve at a 16 mm diameter around the cornea center. The Y-axis 118 is inverted with higher SAG values lower down on each graph. All four graphs above have the same Y-axis scale.

Figure 3C:
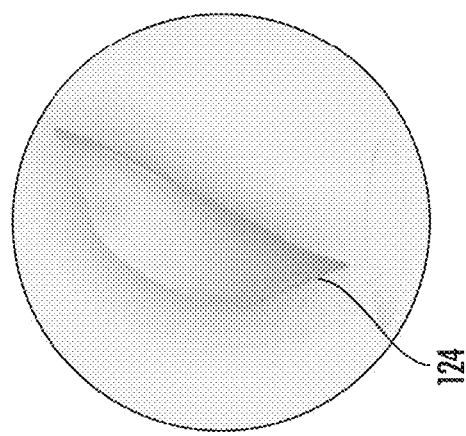
FIG. 3C illustrates a category of sclera shape, asymmetric.
Figure 3B:
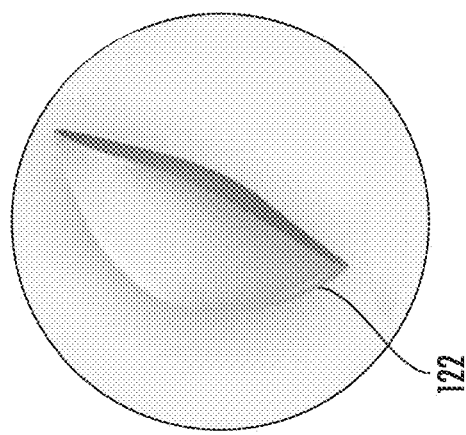
FIG. 3B illustrates a category of sclera shape, toric.
Figure 3A:
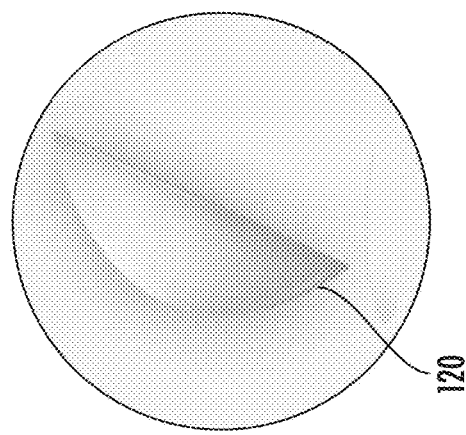
FIG. 3A illustrates a category of sclera shape, spherical.

In evaluating 140 cases scheduled for scleral lens fitting (see SSSG J Cont Lens Res Sci, Vol 191:12-22; Nov. 16, 2017), almost ⅔ of the cases had what was considered an abnormal shape at a radius of 8 mm (16 mm diameter) from the corneal center: 3% having a spherical shape 120 (FIG. 3A, predominately spherical with low amplitude deviations within 300 microns from the highest point to the lowest point); 30% having toric shape 122 (FIG. 3B, predominately toric surfaces conforming to a regular toric curve and sagittal height values within 300 microns from elevation to elevation and depression to depression), and 65% asymmetrical 124 (FIG. 3C, asymmetrical high or low points or periodicity different from 180°). The asymmetric, depression or elevation shape pattern 112 category and the asymmetric, periodicity not 180° pattern 114 category shown in FIG. 2C and FIG. 2D were considered abnormal shapes. Practitioners have recognized the most extreme of these abnormal shapes clinically when they see a substantial difference in fit between areas of the lens 180° apart. As such, customized lenses with differing fit parameters in areas 180° apart, referred to as "quadrant specific" lenses, can be made. Currently, these lenses are only manufactured when a practitioner observes a fit problem clinically or with an instrument that will visualize the scleral shape (see instrument described in U.S. Pat. No. 7,862,178).

In Keratoconus, shape plots may be generated through the high point of the corneal cone, as measured by corneal elevation topography and at an 8 mm radius from the corneal center, which is approximately the position of the edge of a 16 mm diameter scleral lens. In many cases, it was found that the axis of the high point of the corneal cone (point with the smallest SAG value) corresponded to the lowest point of the scleral shape plot at a 16 mm diameter (point with the highest SAG value). This occurred in cases with cones in the inferior portion of the cornea (FIGS. 4A-4C) and cones, and other elevation irregularities on the superior portion of the cornea (FIG. 5A-5C).

FIG. 4A shows a color-coded cornea map 126 demonstrating an inferior cone at approximately 325° and 2 mm from the corneal center. The yellow/red circle 127 represents the location of the cornea irregularity. FIG. 4B illustrates a corneal circumferential shape plot graph 128, at 2 mm radius and demonstrating the high point of the cone at approximately 325°. FIG. 4C illustrates a corresponding scleral circumferential shape plot graph 130, at an 8 mm radius, which demonstrates a low point on the sclera at the axis corresponding to the high point of the cone.

FIG. 5A shows a color-coded cornea elevation map 132 demonstrating a superior elevation due to ectasia with its apex at approximately 90° and 2.45 mm from the corneal center. FIG. 5B shows a circumferential cornea shape plot graph 134, at a 2.45 mm radius, demonstrating the high point of the cone at approximately 90°. FIG. 5C shows a sclera circumferential shape plot graph 136 at an 8 mm radius that demonstrates a low point on the sclera at the axis corresponding to the high point of the cone.

Figures 6A, 6B, 6C:
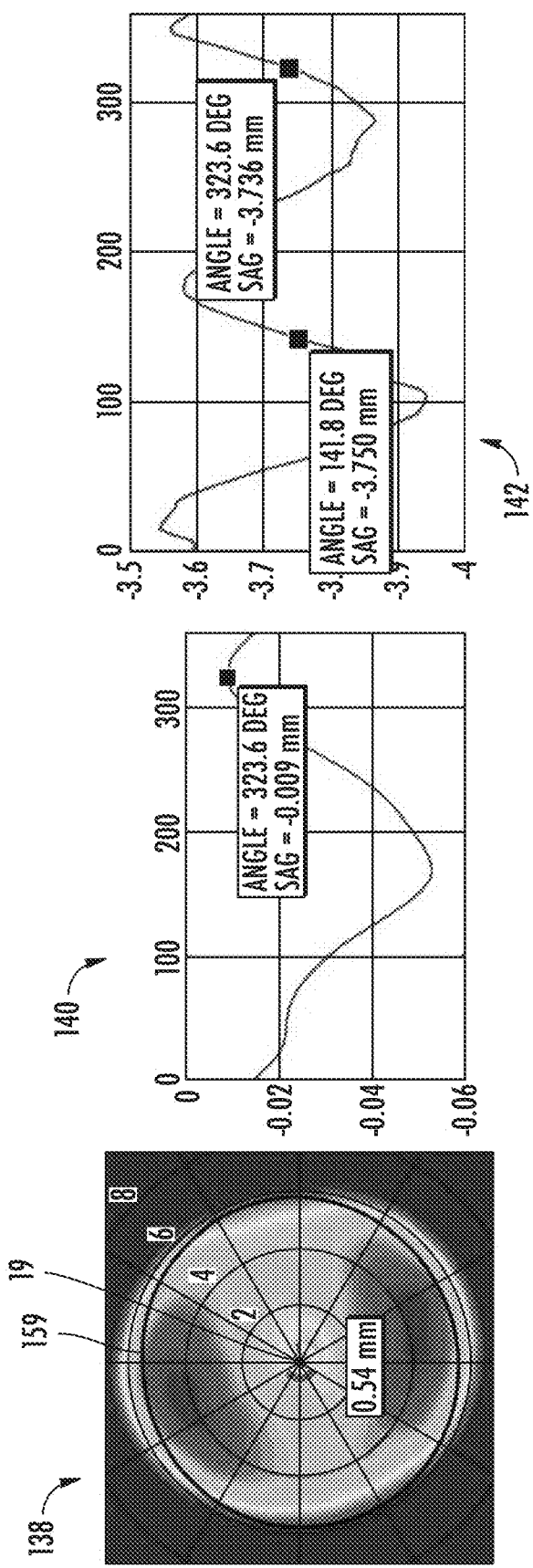
FIG. 6A is a color-coded cornea map with cone apex at 0.54 mm radius.
FIG. 6B is a cornea shape plot graph at 0.54 mm radius.
FIG. 6C is a sclera shape plot graph at 8 mm radius.

Referring to FIGS. 6A-6C, a cone close to the center of the cornea is shown. FIG. 6A shows a color-coded cornea elevation map graph 138 demonstrating a cone close to the center of the cornea with its apex at approximately 325° and 0.54 mm from the corneal center. FIG. 6B shows a cornea circumferential shape plot graph 140 at a 0.54 mm radius, demonstrating the high point of the cone at approximately 325°. FIG. 6C shows a sclera on a circumferential shape plot graph 142, at an 8 mm radius that demonstrates no real correlation between the high point of the cone and the scleral shape. With cones very close to the center of the cornea, this phenomenon (smallest corneal SAG value corresponding to the point with the highest scleral SAG value) occurred with less frequency.

In order to quantitate the relationship described, corneoscleral topography data from two hundred and twenty-seven cases of keratoconus was analyzed. In each case, the exact radius and angular direction was determined (angle in polar coordinates) from the center of the cornea to the apex of the cone, and the sagittal height (SAG) of the eye along this apex angle, and 180° away from it at a 16 mm diameter. The difference in SAG (in microns, µ) between the axis of the apex of the cone and 180° away from it at a 16 mm diameter is referred to as the quadrant specific effect (QSE). Standard toricity (ST) was also studied at the same 16 mm diameter. ST was defined as the difference in SAG from the highest point to the lowest point on the best fit $Sin^2$ curve fitting the scleral shape at that diameter.

For the whole series, the QSE was 207±18 µm while ST was 217±9 µm. The difference between QSE and ST was not significantly different (p>0.05). Numbers separated by a ± sign represented mean values±standard error. In the 37% of the population where the cone apex was located <1.25 mm from the corneal center, QSE was 66±24 µm while ST was 210±15 µm, a highly significant difference (p<0.001). In the remaining 63% of the irregular cornea population where the cone apex was located ≥1.25 mm from the corneal center, the QSE was 289±22 µm while ST was 220±11 µm, a significant difference (p<0.01). While the difference in ST between the <1.25 mm and ≥1.25 mm groups was not significantly different (210±15 µm vs. 220±11 µm, p>0.05), the difference in QSE was significantly different (66±24 µm vs. 289±22 µm, p<0.001). In the cases where the radius of the cone apex was >1.25 mm from the corneal center, 61% had QSE>200 µm, 45% showed a difference of >300 µm and 28% had a >400 µm difference. These results suggest that quadrant specific lenses from a fitting set be tried for any case with the cone apex >1.25 mm away from the central cornea. As an example, two sizes of quadrant specific lenses may be used; one with 200 µm of SAG between two axes 180° away from each other, and one with 300-400 µm of SAG between two axes 180° away from each other. Given the values above, the expectation would be that, in many cases, the quadrant specific fitting set lenses would align to the ocular surface better than standard spherical or toric fitting set lenses. While in the example above, only data from shape plots at a 16 mm diameter from the corneal center was utilized, the design of a quadrant specific fitting set lens may be further refined by also utilizing data from other diameters from the center, such as 7 mm and 7.5 mm from the corneal center.

Figure 7B:
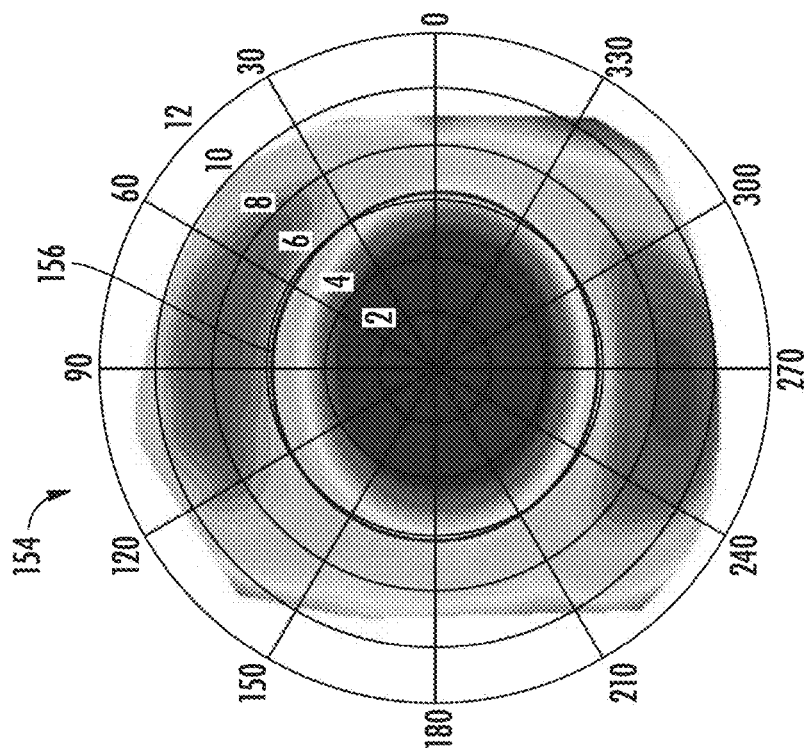
FIG. 7B is a scleral elevation topography.
Figure 7A:
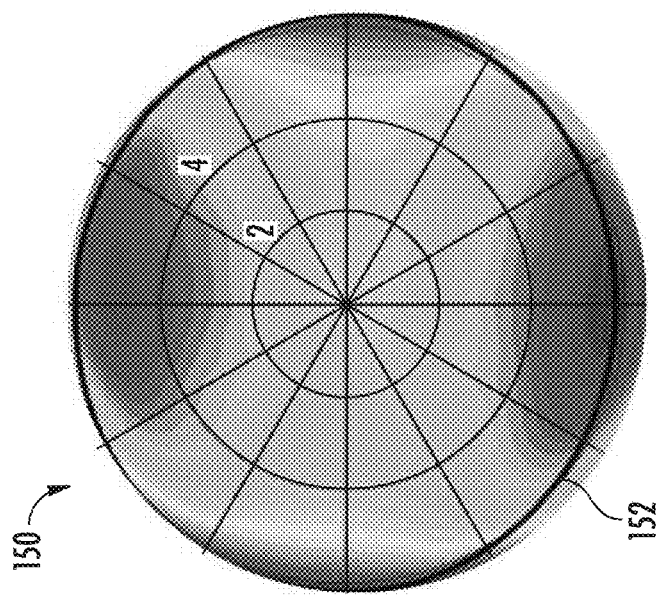
FIG. 7A is a corneal elevation topography.

Additional support for methods which utilize patterns observed on a corneal topography examination to improve the fit of scleral lenses was found in cases with high corneal astigmatism. FIG. 7A is a color-coded cornea elevation topography map 150 demonstrating with-the-rule astigmatism with the steeper axis vertical. The black circle 152 in the periphery is the ocular limbal region. FIG. 7B is a color-coded scleral elevation topography map 154. The color-coded scleral elevation topography map 154 also demonstrates with-the-rule astigmatism with the steeper axis vertical. The black circle 156 in the middle of the map is the ocular limbal region (limbus represents the extreme periphery of the cornea). The scleral topographic astigmatic pattern was shown to "follow" the corneal pattern, also showing a vertical steepening, which has implications on scleral lens fitting.

Figure 8B:
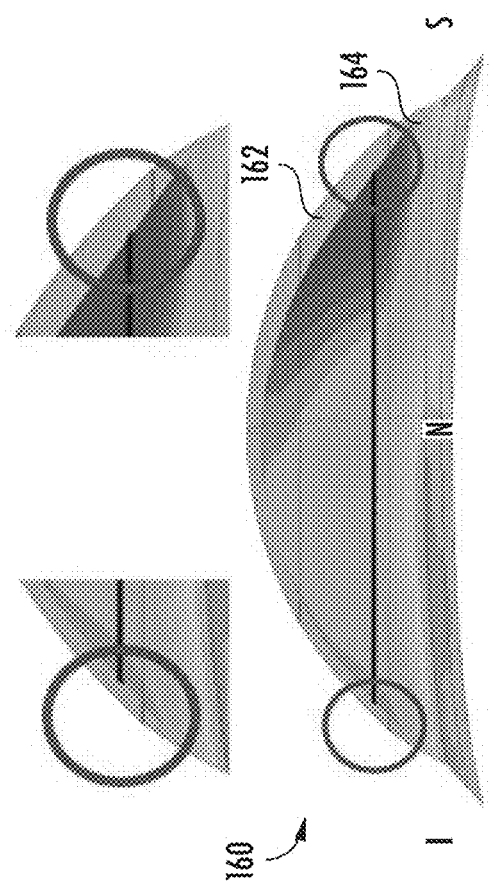
FIG. 8B is a lens elevation map, sagittal view through steep axis.
Figure 8C:
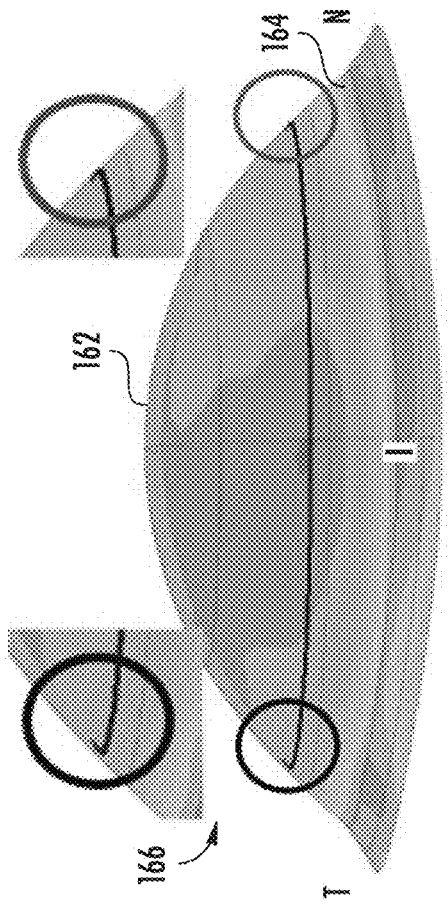
FIG. 8C is a lens elevation map, sagittal view through flat axis.
Figure 8A:
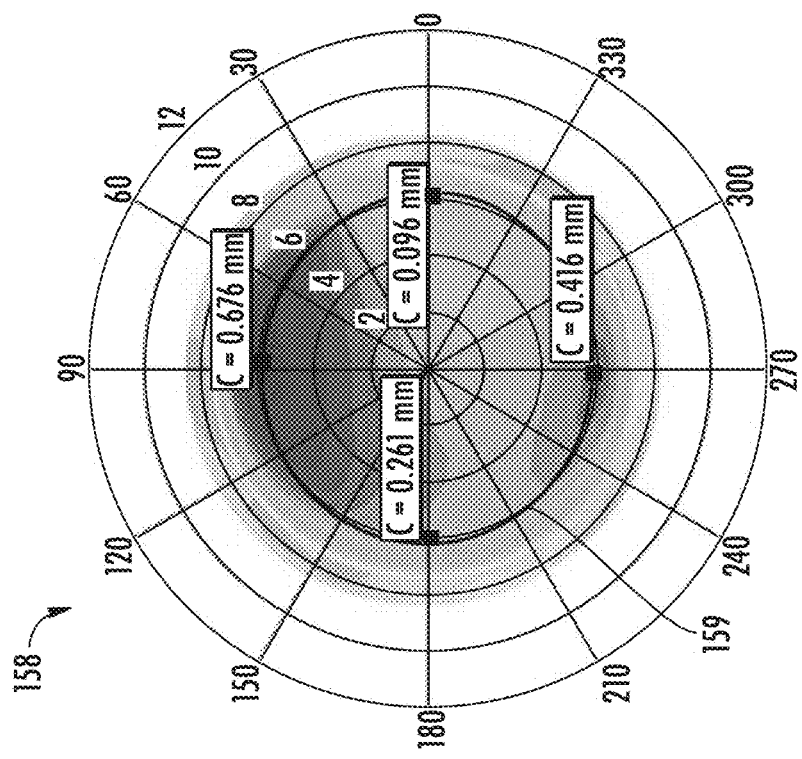
FIG. 8A is a lens elevation map, anterior view.

FIG. 8A demonstrates an anterior view of a color-coded lens elevation map 158 (of the same case shown in FIGS. 8A/B) showing the fit of a standard scleral lens to the ocular surface. The numbers along the periphery represent limbal clearances in mm at 0, 90, 180 and 270 degrees. The black circle 159 is the ocular limbal region. FIG. 8B illustrates a sagittal view 160 through the vertical meridian of the lens 162 and eye 164 (steep axis of astigmatism) showing excessive limbal clearance, especially superiorly (s). FIG. 8C is a sagittal view 166 of the horizontal meridian. FIG. 8C demonstrates that, in the horizontal meridian of the lens 162 and eye 164 (flat axis of astigmatism), the limbal clearances (nasally (n) and temporally (t)) are much closer to optimal (normal clearance).

Figure 9A:
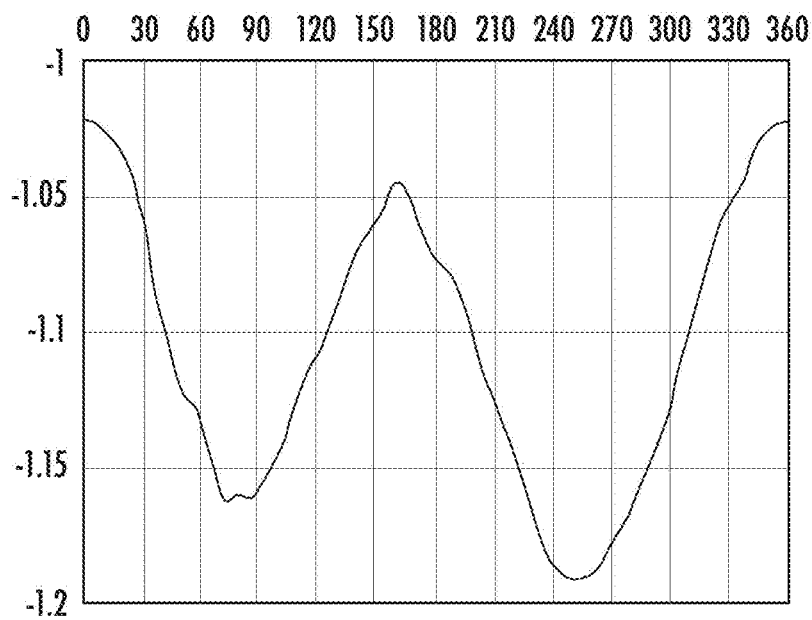
FIG. 9A is a corneal shape plot at 4 mm from the corneal center.
Figure 9B:
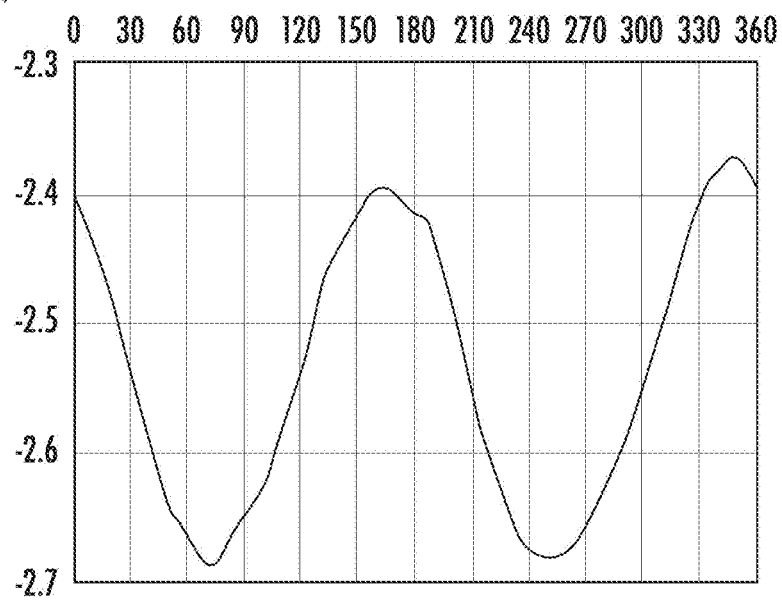
FIG. 9B is a scleral shape plot at the limbus at 6 mm from the corneal center.

FIG. 9A is a corneal shape plot 165 at a 4 mm radius from the center of the cornea. FIG. 9B is a scleral shape plot 167 at a 6 mm radius near the limbus. The fact that the scleral shape "follows" the corneal shape is reflected in the similarity of the corneal and scleral shape plots.

In a study of eight patients demonstrating relatively high degrees of with-the-rule astigmatism, the average limbal SAG in the vertical meridian was 413 microns vs. 169 microns in the horizontal meridian, demonstrating an amount of regular toricity averaging 244 microns. Furthermore, the average limbal SAG superiorly was 491 microns vs. 336 microns inferiorly, a difference of 155 microns in quadrant specific toricity vertically. The average limbal SAG nasally (horizontally in the area closest to the nose) was 180 microns vs. 159 microns temporally (horizontally in the area closest to the temple), a difference of 21 microns in quadrant specific toricity horizontally. These findings support hypothesis that one or a number of customized diagnostic fitting set lens(es) can be designed to better fit these highly astigmatic eyes instead of the standard fitting set lenses that are generally spherical over the limbal portion of the lens. The best average fit of these eight eyes would have 244 microns of regular scleral toricity, and also have quadrant specific toricity with the superior portion of the lens being 155 microns steeper than the inferior portion and the nasal portion being 21 microns steeper than the temporal portion. The data may be stratified by a number of variables, such as amount of corneal toricity measured by corneal topography or refraction, to refine the changes needed in the proposed fitting set lenses. This same analysis can be applied to the fit past the limbus in the scleral landing zone.

Figure 10:
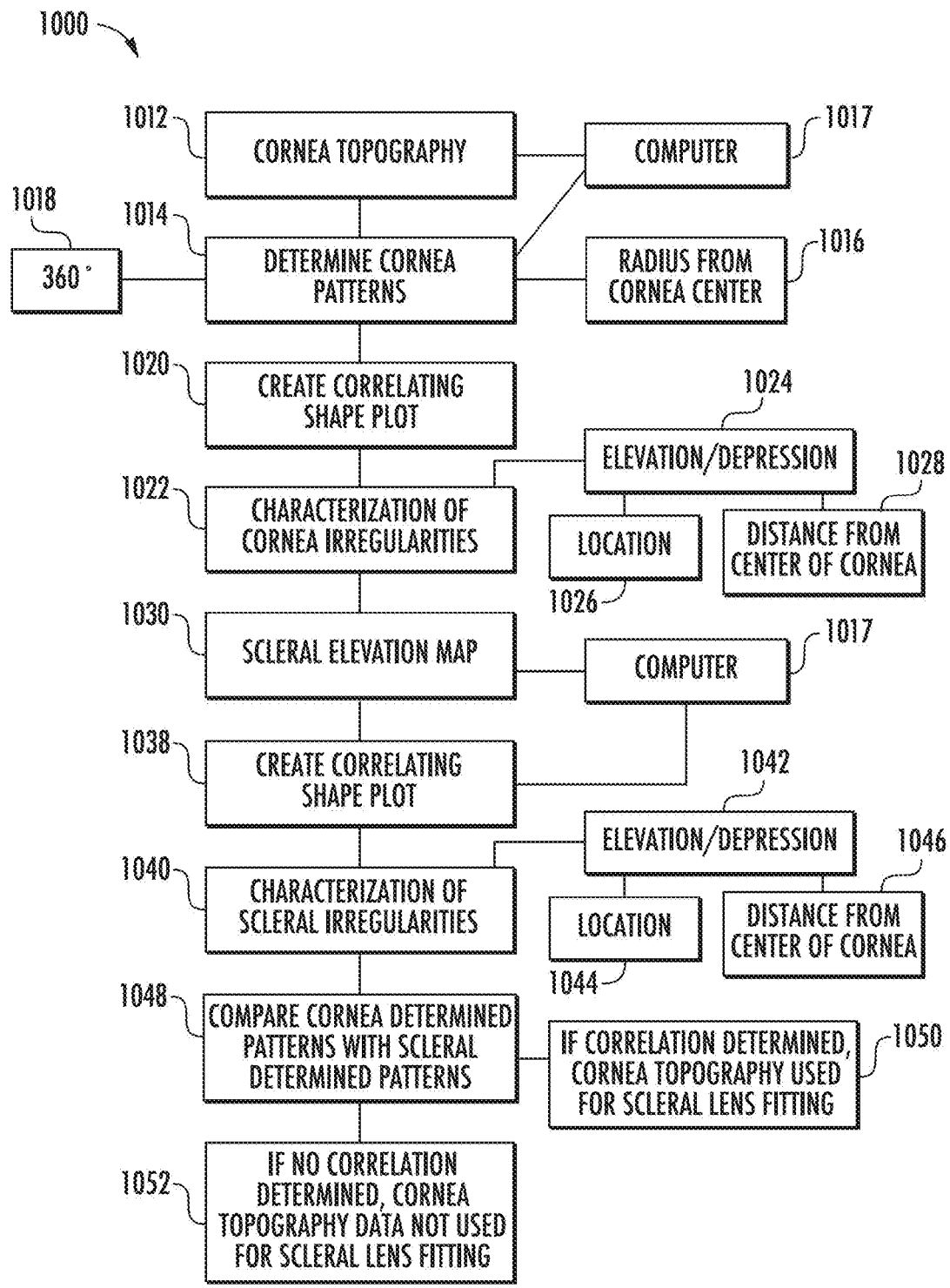
FIG. 10 is a flow chart representing an illustrative embodiment of a method of determining if cornea information may be used for fitting scleral or corneo-scleral lenses.
Figure 11:
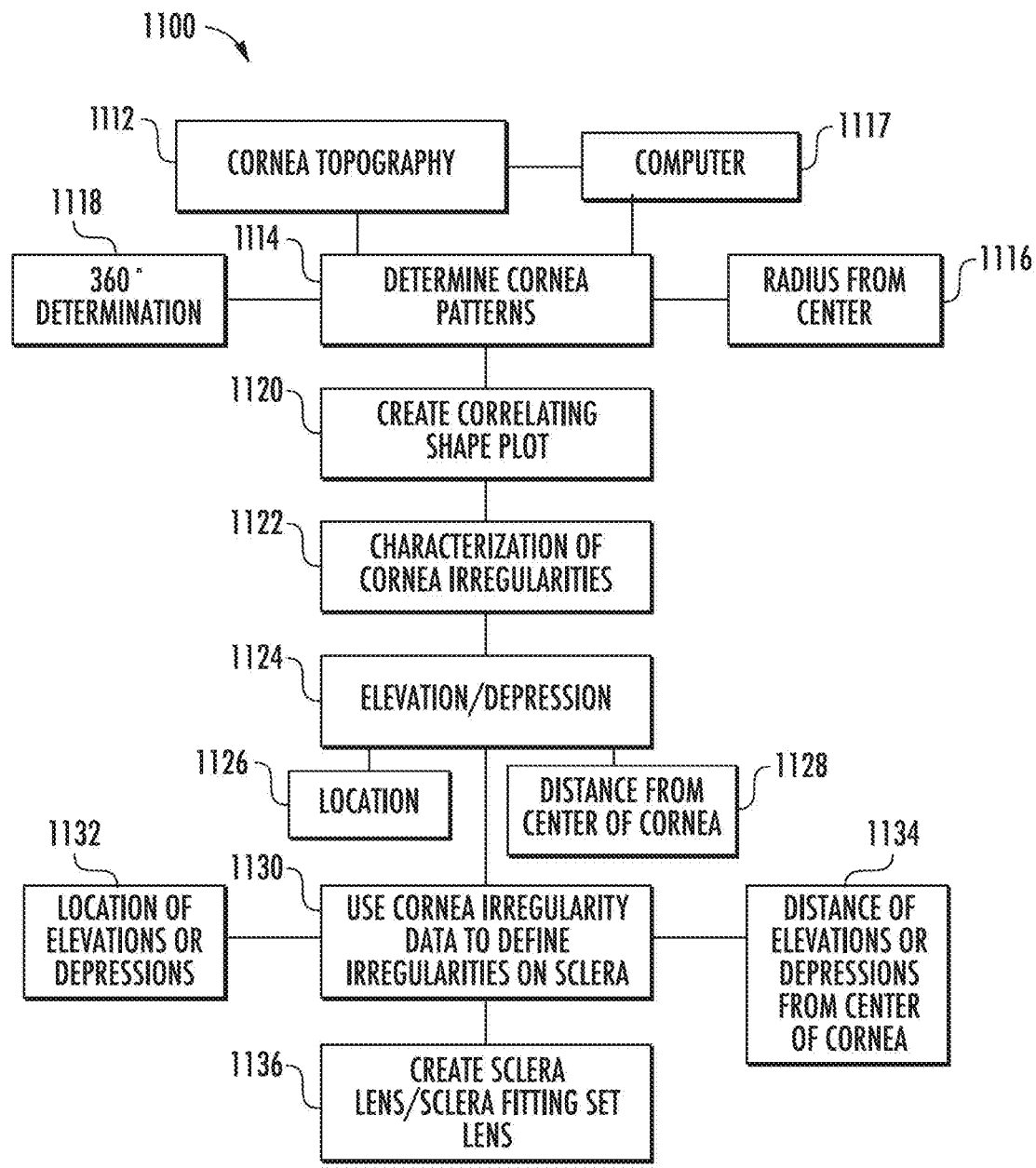
FIG. 11 is a flow chart representing an illustrative embodiment of a method of fitting scleral or corneo-scleral lenses using corneal topography.

The data analysis and methods of obtaining such data or information described above provide support for 1) a unique method of determining if cornea information may be used for fitting scleral or corneo-scleral lenses, referred to generally as scleral/corneo-scleral lens fitting determination process 1000, steps outlined in FIG. 10, or 2) a unique method of fitting scleral or corneo-scleral lenses, referred to generally as a scleral/corneo-scleral fitting process 1100, steps outlined in FIG. 11. Any of the steps used, described, or outlined above, in any combination or configuration, if not described below, can be incorporated into either of following processes: scleral/corneo-scleral lens fitting determination process 1000 or scleral lens fitting process 1100.

Referring to FIG. 10, an illustrative embodiment of a scleral/corneo-scleral lens fitting determination process 1000 is illustrated. The unique scleral/corneo-scleral lens fitting determination process 1000 provides information which can be used by eye care professionals to determine if patterns observed on a corneal topography examination for various types of eye irregularities can be used to improve the fit of scleral lenses or corneo-scleral lenses. The scleral/corneo-scleral lens fitting determination process 1000 starts by obtaining or determining information from a cornea topography map, see step 1012, similar to the map shown in FIG. 6A. A cornea topography map may be generated (via a topography imaging device), or a pre-existing cornea topography map may be used. Typically, a cornea topography map plots the power of the cornea, but with mathematical manipulations can also determine the height of the eye surface, between 0° and 360° from the center of the cornea. The cornea topography map plots and identifies high points, representing surface elevations, and low points, representing surface depression. These elevations or depressions represent irregulates in the cornea shape.

From the cornea topography map, surface patterns (peaks and valleys) are determined, step 1014, at one or more distances from the center of the cornea, step 1016, and from 0° to 360°, see step 1018. Analysis may be aided by use of a computer 1017 (hardwired or wireless via, for example, WIFI or BLUETOOTH technology), having the necessary hardware for processing capability (processor), storage capability and any necessary software to drive or control the functioning of various components, scanning or analysis; and may include, for example, logic boards such as printed circuit boards with the necessary integrated circuitry, central processing units, memory, RAM, ROM, and/or hard drives. As illustrated in the examples described previously (FIGS. 4A-7A), the distance may be close to the corneal center, out near the limbus, close to a 6 mm radius from the center of the cornea, or anywhere in between. This pattern is best observed using a cornea shape plot made by graphing the sagittal height of the eye (SAG, Y-axis) against the meridional axis (X-axis) 360° for any radius or diameter from the center of the cornea within a 12 mm diameter from the center of the cornea depending on the observed changes in the color map (FIGS. 4A-7A). The corneal shape plot can be defined at a fixed distance from the corneal center up to a diameter of 12 mm, or the distance from the center may vary in individual cases based on the distance of any corneal elevation or depression from the corneal center. The characteristics of the corneal pattern can be defined by the presence of elevations or depressions (1024), their location on a circle 360° around (1026), and their distance from the center of the cornea. The pattern, determined within the center circle is correlated to a pattern associated with the sclera. One can next observe the scleral elevation map (FIG. 1A, 1030) defining the pattern of elevations and depressions (1024), defining scleral patterns based upon their location on a circle 360° around, and their distance from the center of the cornea. The characterization of scleral irregularities is best determined using a scleral shape plot made by graphing the sagittal height of the eye (SAG, Y-axis) against the meridional axis (X-axis) 360° for any radius or diameter from the limbus (a 12 mm diameter) to the edge of measurable sclera/conjunctiva (up to 24 mm diameter). The scleral shape plots are typically measured at a given radius from the corneal center, such as 8 mm, although as part of the analysis comparing corneal and scleral shapes, scleral shape plots with radii such as 7 mm, 7.5 mm, and 8 mm may each be analyzed separately against the corneal shape plot data. The scleral shape plots may be generated via use of a computer 1017. The next major step is to compare the observed individual corneal pattern in a series of similar types of cases to the individual scleral pattern and determine if a correlation exists between the corneal and scleral patterns (1048). If a correlation exists, whether positive or negative, between the corneal and scleral shape patterns, then further data analysis can quantitate the relationship to design a specialized scleral lens peripheral fitting lens which may be superior to standard spherical of toric diagnostic fitting set lenses currently in use (1050). If no correlation exists or is observed between cornea and scleral shape patterns in the face of a specific corneal pattern or disease process, then the corneal topography data is not utilized to improve scleral lens fit (1052).

Once the cornea irregularities are defined and characterized, a determination is made if patterns observed on a corneal topography examination for various eye irregularities can be used to improve the fit of scleral lenses or corneo-scleral lenses through analysis and correlation using a scleral topography map. A scleral topography map, similar to the map illustrated in FIG. 1A, may be generated, or a pre-existing scleral topography map may be used, see step 1030. Typically, a scleral topography map is a color-coded map demonstrating the height of the eye surface associated with the scleral, between 0° and 360° at a fixed diameter from the center of the cornea. The scleral topography map can be quantitated using the scleral shape plot which identifies high points, representing scleral surface elevations, and low points, representing scleral surface depressions at a fixed distance from the center of the cornea. These elevations or depressions represent irregularities in the scleral shape.

To determine if the patterns observed on a corneal topography examination for various types of eye irregularities can be used to improve the fit of scleral lenses or corneo-scleral lenses, the data and patterns obtained from the cornea topography map/shape plots can be compared with the data and patterns obtained from the scleral topography map/shape plots, see step 1048. For example, the analysis may entail analyzing the corneo-scleral topography data to determine the exact radius and angular direction (angle in polar coordinates) from the center of the cornea to the apex of the cone, and the sagittal height (SAG) of the eye along this apex angle and 180° away from it at a 16 mm diameter.

From the scleral topography map, surface patterns may be determined at one or more distances from the center of the cornea but on the scleral surface and from 0° to 360°. As illustrated in the examples described previously, the distance may be an 8 mm radius (16 mm diameter). However, any value may be used, for example, any distance greater than 6 mm (limbal area) to 12 mm radius (greater than 12 mm to 24 mm diameter). From this data obtained, a correlating scleral shape plot (similar to the shape plot illustrated in FIG. 1B) is created, see step 1038. The data obtained from the correlating scleral shape plot is used to characterize the irregularities of the scleral, see step 1040. These irregularities are defined on the shape plot as elevations or depressions, see step 1042, with the location, see step 1044, and/or the distance from the cornea, step 1046, being determined.

As an example of how the invention was implemented, a large number of corneal topography maps, such as those seen in FIGS. 4A, 5A and 6A, and the corresponding corneal shape plots, such as those shown in FIGS. 4B, 5B and 6B, in patients with keratoconus, was observed. In these and other keratoconus cases, the corneal shape plot was compared to the scleral shape plots (shown in 4C, 50 and 6C). In most of the cases where the highest elevation of the cornea was not in the corneal center (like 4A and 5A), the corneal and scleral shapes appeared inverted (the areas of depression on the cornea are the same axis as areas of elevation on the sclera (compare 4B and 4C as well as 5B and 5C). We further recognized that a scleral shape pattern, such as seen in 4C and 5C, would require a specialized quadrant specific lens to fit that scleral shape. Furthermore, we observed that in those cases where the highest elevation of the cornea was in the corneal center (similar to FIG. 6A), that inverted relationship between corneal and scleral elevation maps was not present, and that a less customized and more standard lens would fit the sclera. Given these observations in individual cases, we collected a large database of keratoconus cases (227 cases) that underwent corneal and scleral topography, and determined how far away from the corneal center and in what direction the highest elevation of the cornea was on the corneal topography map. We then collected scleral shape plots at an 8 mm radius from the corneal center and calculated the amount of quadrant specific toricity in the axis of the highest elevation of the cornea and at a point 180° away from the highest elevation. As expected, those cases with corneal elevation not in the center of the cornea (>1.25 mm from the corneal center) had much more quadrant specific toricity (289p) than those with central elevations (66p). This methodology allows us to design a specialized diagnostic fitting set lens that would better fit patients with these types of non-central corneal elevations.

Another example of the application of this method is found in patients with high corneal astigmatism. In the eight cases we studied, all had similar appearing corneal (FIG. 7A) and scleral elevation (FIG. 7B) maps with (blue) areas of depression vertically. This is different from the previous example where, in keratoconus cases, the corneal and scleral shape plots appeared inverted. These depressed areas of the ocular surface vertically resulted in excessive clearance of a standard scleral lens vertically (FIGS. 8A and 8B), while clearance was normal horizontally (FIGS. 8A and 8C). The similarity between corneal (FIG. 9A) and scleral (FIG. 9B) areas is shown best on the shape plots 165,167. The depressions vertically can be observed on the x-axis of both plots at approximately 90° and 270°. By simply collecting sagittal height (SAG) data on cases with high astigmatism at the elevations and depressions, that data can be used to define the amount of standard toricity and quadrant specific toricity needed on a special diagnostic fitting set lens or lenses to best fit these types of cases.

The unique method, referred to generally as the scleral/corneo-scleral fitting process 1100, utilizes patterns observed on a corneal topography examination to improve the fit of scleral lenses or corneo-scleral lenses. Referring to FIG. 11, an illustrative embodiment of the scleral/corneo-scleral fitting process 1100, is illustrated. The scleral/corneo-scleral fitting process 1100 starts by obtaining or determining information from a cornea topography map, see step 1112, similar to the map shown in FIG. 7A. A cornea topography map may be generated, or a pre-existing cornea topography map may be used. Typically, a cornea topography map plots the height of the eye surface, between 0° and 360° from the center of the cornea. The cornea topography map plots and identifies high points, representing surface elevations, and low points, representing surface depressions. These elevations or depressions represent irregulates in the cornea shape.

From the cornea topography map, surface patterns are determined, step 1114, at one or more distances from the center of the cornea, step 1116, and/or from 0° to 360°, see step 1118. Analysis may be aided by use of a computer 1117 (hardwired or wireless via for example WIFI or BLUETOOTH technology), having the necessary hardware for processing capability (processor), storage capability and any necessary software to drive or control the functioning of various components, scanning or analysis; and may include, for example, logic boards such as printed circuit boards with the necessary integrated circuitry, central processing units, memory, RAM, ROM, and/or hard drives. Any value may be used, for example, any distance greater than 0 mm to 6 mm radius (greater than 0 to 12 mm diameter). From this data obtained, a correlating cornea shape plot is created (similar to FIG. 4B, see step 1120. The correlating cornea shape plot may be made by graphing the sagittal height of the eye (SAG, Y-axis) against the meridional axis (X-axis) 360° for any radius or diameter from the center of the cornea. The data obtained from the correlating cornea shape plot is used to characterize the irregularities of the cornea, see step 1122. These irregularities are defined on the shape plot as elevations or depressions, see step 1124, with the location, see step 1126, and/or the distance from the cornea, step 1128, being determined. The SAG was also determined.

The data relating to the characterizations of the irregularities are then used to define the irregularities in the sclera, see step 1130. For instance, based on the elevations/depressions in the cornea, the SAG value, locations and distances from the center of sclera elevations and depressions can be determined in the sclera, see steps 1132 and 1134. As shown in FIG. 4B, the cornea highest point elevation was characterized to be around 320°. This elevation corresponds to the sclera lowest point depression being around 320°. Thus, using only the cornea topography, eye care practitioners would be able to map out an irregularity of a low point at the corresponding point in the sclera. As shown in FIG. 5B, the lowest point on the cornea was determined to be at 90°. The depression would correspond to the highest point on sclera at 90°. Thus, using only the cornea topography, eye care practitioners would be able to map out an irregularity of a high point at the corresponding point in the sclera. As shown in FIG. 6B, the low point on the cornea at around 320° was characterized. This depression would correspond to the high point on the sclera at around 320°. Thus, using only the cornea topography, eye care practitioners would be able to map out an irregularity of a high point at the corresponding point in the sclera.

Such data can be used to create scleral or corneo-scleral lens or scleral or corneo-scleral fitting lens sets, step 1136. From the cornea eye patterns, the eye care professional knows where corresponding eye irregularities, i.e. elevations and depressions, in the sclera would be located and would be able to fit (shape, location and height) scleral or corneo-scleral irregularities. Alternatively, one or more scleral or corneo-scleral lenses, which are designed to accommodate the size, shape, location, or other characteristics of the irregularities, may be provided to an individual in need, such as part of a testing kit.

Scleral/Corneo-Scleral Fitting Lens/Lens Sets.

Figure 12:
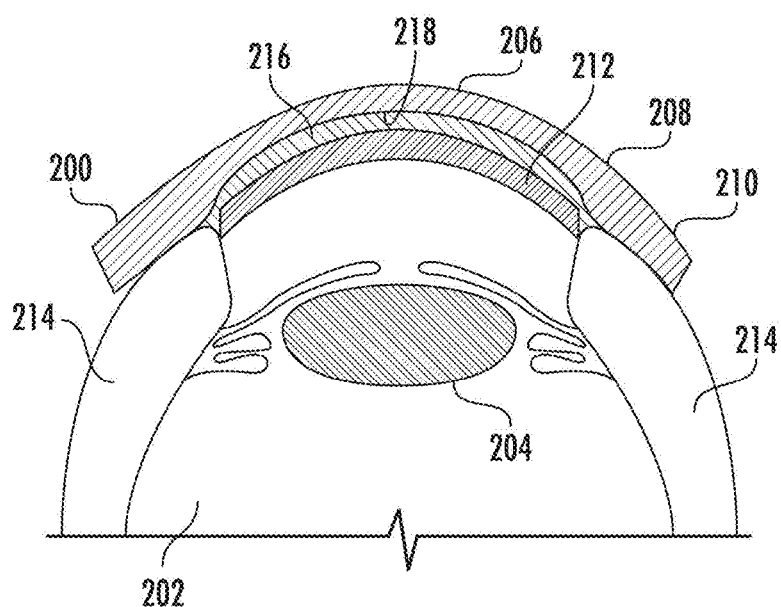
FIG. 12 is a schematic illustrating a standard symmetrical sclera lens applied to an eye, elevated above the cornea and resting on the sclera.

One or more lens may be included in a diagnostic of lens fitting set. FIG. 12 illustrates a standard sclera lens 200 placed on the eye 202, with the center circle 204 representing the lens. The clear lens comprises an optical zone 206, a transition zone 208 (from edge of optical zone to landing zone), and a landing zone 210 (area of contact with optical surface of the sclera). The optical zone 206 is shown vaulted over the cornea 212 and the landing zone 210 resting on the sclera 214. A liquid reservoir 216 may be positioned between the back surface 218 of the sclera lens and the cornea 212.

Tables 1 and 2 (below) are results of a retrospective study to determine the relationships between corneal and scleral elevation topography in subjects with corneal ectasias and normal corneas. Ocular surface topography (sMap3D, Precision Ocular Metrology, US) was collected on 115 eyes with prolate cornea profile (Group A) and 227 eyes showing corneal ectasia (Group B), see G. DeNaeyer, D. Sanders, et al., Correlation of Corneal and Scleral Topography in Cases With Ectasias and Normal Corneas: The SSSG Study, J Cont Lens Res Sci, Vol 391):e10-e20, May 9, 2019, the content of which is herein incorporated by reference.

TABLE 1

QSE, ST and RMSE Findings for Groups A and B

| Parameter Studied @ 16 mm Chord | Group A (Mean ± Standard Error in μm) | Group B (Mean ± Standard Error in μm) | p-Value-Group A vs B |
|---|---|---|---|
| QSE | 17 ± 20 | 207 ± 18 | p < 0.001 |
| ST | 172 ± 9 | 217 ± 9 | p < 0.001 |
| RMSE | 96 ± 5 | 133 ± 5 | p < 0.001 |

TABLE 2

The Effect of Corneal Apex Position on QSE, ST and RMSE.

| Parameter Studied @ 16 mm Chord | Group B2 (Mean ± Std Error in μm) | p-Value vs. Group A | Group B3 (Mean ± Std Error in μm) | p-Value vs. Group A | p-Value Group B2 vs. B3 |
|---|---|---|---|---|---|
| QSE | 66 ± 24 | p > 0.05 | 289 ± 22 | p < 0.001 | p < 0.001 |
| ST | 210 ± 15 | p = 0.028 | 220 ± 11 | p > 0.001 | p > 0.05 |
| RMSE | 101 ± 5 | p > 0.05 | 151 ± 6μ | p > 0.001 | p < 0.001 |

Table 1 summarizes the findings of this study. These results indicate significant differences between both groups, based on average quadrant specific effect (QSE) (A: 17±20 μm vs. B: 207±18 μm; p<0.001) and standard toricity (A: 172±9 μm vs. B: 217±9 μm; p<0.001). In Group A, the QSE was not significantly greater than zero (p>0.05), while it was significant in group B (p<0.001). QSE versus standard toricity (ST) was found significant for group A (difference of 45 μm), while the small variation in group B (10±20 μm) was not found statistically different. The RMSE value in group A was lower than in the group B (96±5 μm vs. 133±5 μm; p<0.001).

It was interesting to note that QSE was not easily demonstrated if the apex was located <1.25 mm from the corneal center, a subgroup of subjects (Group B2) constituting 37% of the irregular cornea population (Table 2). In fact, for these subjects, QSE and RMSE value were not significantly different from group A (p>0.05). ST was statistically lower in group A vs. B2 (p=0.028). In Group B2, the average standard toricity was 210±15 μm and QSE was 66±24 μm, which represents a significant difference between these two values (p<0.001). The B2-RMSE value was 101±5 μm, not significantly higher than group A (96±5 μm, p>0.05). The remaining 63% of the irregular cornea population were cases where the apex was located 1.25 mm from the corneal center (Subgroup B3). This reasonably obvious dividing point between groups B2 and B3 at approximately 1.25 mm was observed by visual observation of the QSE and RMSE variables as the distance from the apex increased. Table 2 provides side-by-side findings, allowing comparison of Group B2 versus B3. QSE and RMSE were significantly different (p<0.001), reflecting more asymmetry in the latter group; ST was found similar in both groups (p>0.05). QSE was strongly present if apex location was >1.25 mm from the corneal center. QSE reached 289±22 μm, significantly different than group A (p<0.001). A majority of B3-subjects (61%) had QSE>200 μm, 45% showed a difference of >300 μm and 28% had >400 μm difference. ST was evaluated as 220±11 μm, again statistically different than group A (p=0.001). This subgroup was the only ectatic group showing ST being significantly less than QSE (−69±26μ, p<0.01). Finally, the B3-RMSE value was 151±6 μm, significantly higher than group A (96±5, p<0.001). A significantly greater proportion of ectasia cases were found in the groups with irregular sclera shapes (Groups 3 and 4, 129/227 [57%]) compared to prolate corneas (29/115 [25%], p<0.001). Patients graded as having regular conjunctival/scleral shape (Groups 1 and 2) had significantly lower RMSE values than those graded as having irregular shapes (Groups 3 and 4), in both the cases with corneal ectasias (85±4 μm vs. 169±6 μm, p>0.001) and the cases with normal corneas (78±27 μm vs. 150±15 μm, p>0.001).

The data obtained from these studies provides support for unique scleral/corneo-scleral fitting lens/lens sets. Table (group B2) illustrates a non-significant amount of quadrant specific effect (QSE) averaging 66p, with a standard error of 24 p. This implies that the upper 95% confidence limit of the average QSE in these cases with non-significant QSE is the average plus two standard errors or 66+2*24 or 114μ. This number was based upon the data at a 16 mm diameter (8 mm radius).

Figure 13:
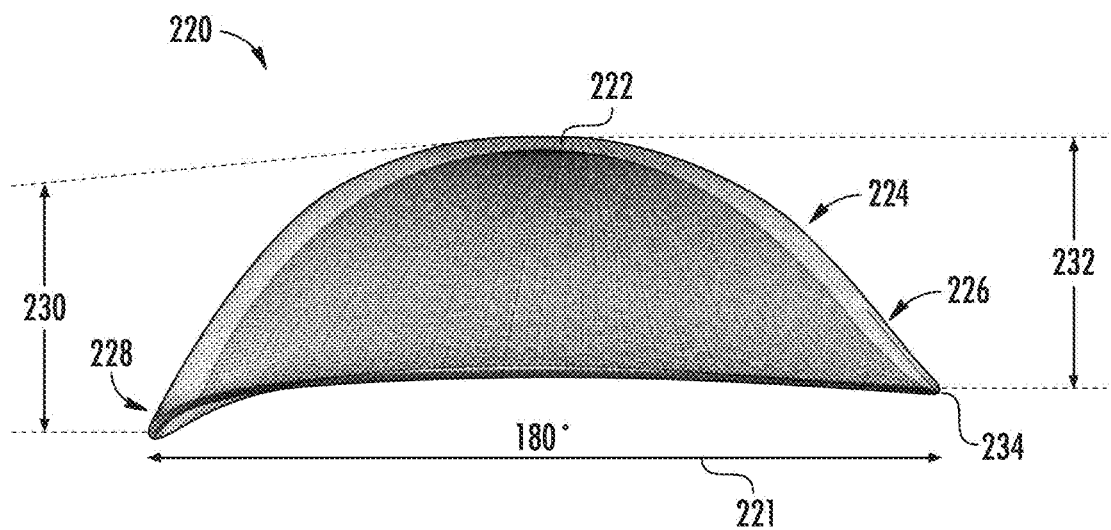
FIG. 13 is an illustrative example of a quadrant specific sclera lens.

Referring to FIG. 13, an embodiment of a sclera lens, illustrated as a quadrant specific (referring to sagittal height changes of two points 180° apart) lens 220 is shown. The quadrant specific lens 220 has a steep periphery and a flat periphery 180 degrees apart, see double arrow 221. The quadrant specific lens comprises an optical zone 222, a transition/mid peripheral cure 224 (starting at about 8-9 mm diameter), and a landing curve 226 (starting at about 11-12 mm diameter). The quadrant specific lens 220 illustrates a steep area 228, having a higher sagittal height 230 (therefore lens is positioned further down on eye) than the sagittal height 232 of the flat area 234. Preferably, the quadrant specific lens 220 includes any lens that has 60.1 to 500p, most preferably at least 100μ or more difference in sagittal height on the back surface of the quadrant specific lens 220 in any two points 180° apart, equidistant from, and at least 5.5 mm from the corneal center. Preferably, the quadrant specific lens 220 includes any lens that has at least 100.1 in sagittal height on the back surface of the quadrant specific lens 220 in any two points 180° apart, equidistant from, and at least 5.5 mm from the corneal center. Accordingly, the quadrant specific lens 220 can be defined by any portion of the surface in which any two points or axis, 180° apart, have difference in sagittal height, preferably of 100u.

Figure 14:
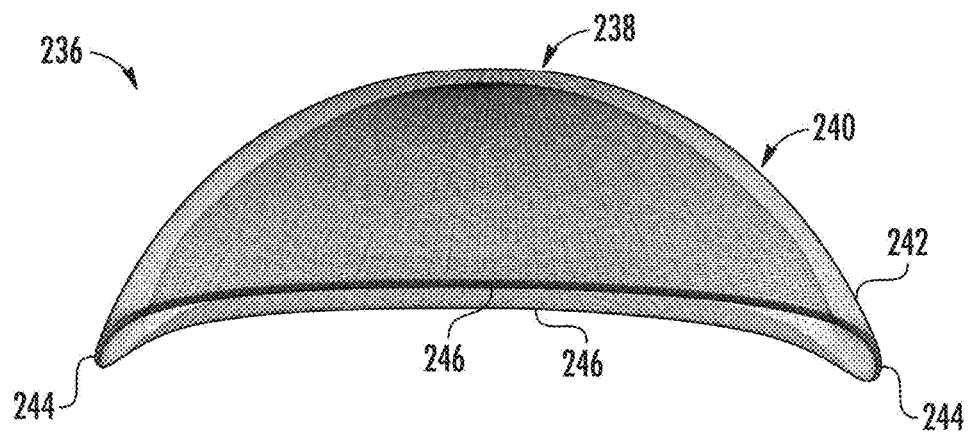
FIG. 14 is an illustrative example of a toric fitting sclera lens, with the toricity applied in the mid peripheral area.
Figure 15:
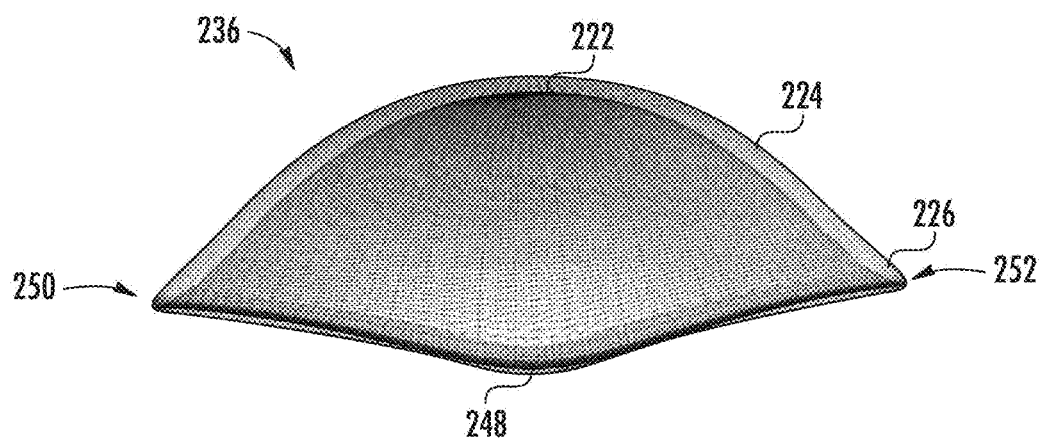
FIG. 15 is an illustrative example of a toric fitting sclera lens, with the toricity applied over the cornea.

Referring to FIG. 14, an embodiment of a sclera lens, illustrated as a toric (referring to sagittal height changes of two points 90° apart) fitting lens 236. The toric fitting lens 236 comprises an optical zone 238, a transition/mid peripheral curve 240 (starting at about 8-9 mm diameter), and a landing zone 242 (starting at about 11-12 mm diameter). The toric fitting lens 236 illustrates a steep area or axis 244 and a flat area or axis 246. In this embodiment, the toricity is applied in the mid peripheral area (over the cornea). The toric fitting lens 236 begins the toric curve over the cornea in the mid peripheral area. Preferably, the toric fitting lens 236 includes any lens that has 60μ to 500p, most preferably at least 100μ or more difference in sagittal height on the posterior (or back surface) lens surface in any two points 90° apart, equidistant from (preferably from cornea center), and within 5 mm from the corneal center. Toricity begins central to the landing zone 244. Preferably, the toric fitting lens 236 includes any lens having at least 100μ in sagittal height on the posterior) lens surface in any two points 90° apart, equidistant from (preferably from cornea center), and within 5 mm from the corneal center. Accordingly, the toric fitting lens 236 can be defined by any portion of the surface in which any two points or axis, 90° apart, have difference in sagittal height, preferably of 100u. FIG. 15 illustrates a toric fitting lens 236 where the toricity is applied over the cornea. As illustrated, the toric fitting lens 236 comprises a steep axis or area 248 and flat axis or area 250 and 252.

A sclera lens fitting set or a corneo-scleral lens fitting set may include one or more of the lens described above. As an illustrative embodiment, a sclera lens fitting set may include one quadrant specific lens 220 having at least between 100μ and 199p, preferably 100μ or more difference in sagittal height on the back surface of the quadrant specific lens 220 in any two points 180° apart, equidistant from, and at least 5.5 mm from the corneal center. The sclera lens fitting set may include one quadrant specific lens 220 having at least between 200μ and 299p, preferably 200μ or more difference in sagittal height on the back surface of the quadrant specific lens 220 in any two points 180° apart, equidistant from, and at least 5.5 mm from the corneal center. The sclera lens fitting set may include one quadrant specific lens 220 having at least between 300μ and 399p, preferably 300μ or more difference in sagittal height on the back surface of the quadrant specific lens 220 in any two points 180° apart, equidistant from, and at least 5.5 mm from the corneal center. The sclera lens fitting set may include one quadrant specific lens 220 having at least between 400μ and 499p, preferably 400μ or more difference in sagittal height on the back surface of the quadrant specific lens 220 in any two points 180° apart, equidistant from, and at least 5.5 mm from the corneal center. The sclera lens fitting set may include one quadrant specific lens 220 having at least 500μ or more difference in sagittal height on the back surface of the quadrant specific lens 220 in any two points 180° apart, equidistant from, and at least 5.5 mm from the corneal center.

The sclera lens fitting set may include multiple quadrant specific lens 220, for example, 2-300+, each having differences in sagittal height on the back surface of the quadrant specific lens 220 in any two points 180° apart. For example, the sclera lens fitting set may include may include three quadrant specific lens 220, one having 100μ difference in sagittal height on the back surface of the quadrant specific lens 220 in any two points 180° apart, equidistant from, and at least 5.5 mm from the corneal center, one having 200μ difference in sagittal height on the back surface of the quadrant specific lens 220 in any two points 180° apart, equidistant from, and at least 5.5 mm from the corneal center, and one having 300μ difference in sagittal height on the back surface of the quadrant specific lens 220 in any two points 180° apart, equidistant from, and at least 5.5 mm from the corneal center.

The sclera lens fitting set may include one toric fitting lens 236 having 100μ to 199μ, most preferably 100μ, difference in sagittal height on the posterior lens surface in any two points 90° apart, equidistant from (preferably from cornea center), and within 5 mm (i.e. any distance greater than zero and to about 5 mm) from the corneal center. The sclera lens fitting set may include one toric fitting lens 236 having 200μ to 299μ, most preferably 200μ, difference in sagittal height on the posterior lens surface in any two points 90° apart, equidistant from (preferably from cornea center), and within 5 mm (i.e. any distance greater than zero and to about 5 mm) from the corneal center. The sclera lens fitting set may include one toric fitting lens 236 having 300μ to 399μ, most preferably 300μ, difference in sagittal height on the posterior lens surface in any two points 90° apart, equidistant from (preferably from cornea center), and within 5 mm (i.e. any distance greater than zero and to about 5 mm) from the corneal center. The sclera lens fitting set may include one toric fitting lens 236 having 400μ to 499μ, most preferably 400μ, difference in sagittal height on the posterior lens surface in any two points 90° apart, equidistant from (preferably from cornea center), and within 5 mm (i.e. any distance greater than zero and to about 5 mm) from the corneal center. The sclera lens fitting set may include one toric fitting lens 236 having 500μ or greater difference in sagittal height on the posterior lens surface in any two points 90° apart, equidistant from (preferably from cornea center), and within 5 mm (i.e. any distance greater than zero and to about 5 mm) from the corneal center.

The sclera lens fitting set may include multiple toric fitting lens 236, for example, 2-300+, each having differences in sagittal height on the back surface of the toric fitting lens 236 in any two points 90° apart. For example, the sclera lens fitting set may include three toric fitting lens 236, one having 100μ, difference in sagittal height on the posterior lens surface in any two points 90° apart, equidistant from (preferably from cornea center), and within 5 mm (i.e. any distance greater than zero and to about 5 mm) from the corneal center, one having 200μ, difference in sagittal height on the posterior lens surface in any two points 90° apart, equidistant from (preferably from cornea center), and within 5 mm (i.e. any distance greater than zero and to about 5 mm) from the corneal center, and one 300μ, difference in sagittal height on the posterior lens surface in any two points 90° apart, equidistant from (preferably from cornea center), and within 5 mm (i.e. any distance greater than zero and to about 5 mm) from the corneal center.

The sclera lens fitting set may include a combination of one or more quadrant specific lens 220 and one or more toric fitting lens 236. Additionally, the lens fitting set may include a combination of one or more quadrant specific lens 220 and one or more standard fit lens commercially available, a combination of one or more toric fitting lens 236 and one or more standard fit lens commercially available, or a combination of one or more quadrant specific lens 220, of one or more toric fitting lens 236, and one or more standard fit lens commercially available.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The use of the term "about" is defined as a value 10-20% above or below the value listed.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

What is claimed is:

1. A sclera or corneo-scleral fitting lens set comprising:
   at least one lens comprising a body having an apex, a front surface, and a back surface constructed and arranged to be disposed on an eye, said lens having a difference in sagittal height in any two points that are 180° apart and at least 5.5 mm from the corneal center, of between 60 microns to 500 microns.

2. The sclera or corneo-scleral fitting lens set according to claim 1, wherein said lens includes an optical zone, a transition/mid peripheral zone, and a landing curve.

3. The sclera or corneo-scleral fitting lens set according to claim 1, wherein said difference in sagittal height is on said back surface of said lens.

4. The sclera or corneo-scleral fitting lens set according to claim 1 comprising:
   two or more lens that have at least 100 microns difference in sagittal height on said back surface of said lens in any two points 180° apart equidistant from, and at least 5.5 mm from a corneal center.

5. The sclera or corneo-scleral fitting lens set according to claim 4, further including at least on standard lens fitting.

6. The sclera or corneo-scleral fitting lens set according to claim 1, comprising multiple lens, wherein, at least one lens has a difference in sagittal height in any two points that are 180° apart of between 100 microns and 199 microns; and one or more second lenses having a difference in sagittal height in any two points that are 180° apart of the 200 microns and 299 microns, 300 microns and 399 microns, 400 microns and 499 microns, at least 500 microns, or combinations thereof.

7. A sclera or corneo-scleral fitting lens set comprising:

at least one lens comprising a body having an apex, an anterior surface and a posterior surface constructed and arranged to be disposed on an eye, said lens having a difference in sagittal height in any two points that are 90° apart, equidistant from, and within 5.0 mm from the corneal center of between 60 microns to 500 microns.

8. The sclera or corneo-scleral fitting lens set according to claim 7, wherein said lens includes an optical zone, a transition/mid peripheral zone, and a landing curve.

9. The sclera or corneo-scleral fitting lens set according to claim 7, wherein said difference in sagittal height is on said posterior surface.

10. The sclera or corneo-scleral fitting lens set according to claim 7 comprising:

two or more lens that have at least 100 microns difference in sagittal height on said posterior surface in any two points 90° apart, equidistant from, and within 5 mm from a corneal center.

11. The sclera or corneo-scleral fitting lens set according to claim 10, further including at least on standard lens fitting.

12. The sclera or corneo-scleral fitting lens set according to claim 7, comprising multiple lens, wherein, at least one lens has a difference in sagittal height in any two points that are 90° apart of between 100 microns and 199 microns; and one or more second lenses having a difference in sagittal height in any two points that are 90° apart of between 200 microns and 299 microns, 300 microns and 399 microns, 400 microns and 499 microns, at least 500 microns, or combinations thereof.

* * * * *